United States Patent
Sato

[11] Patent Number: 5,392,774
[45] Date of Patent: Feb. 28, 1995

[54] EMERGENCY RESUSCITATION APPARATUS

[75] Inventor: Toru Sato, Yonago, Japan

[73] Assignee: Nissho Corporation, Osaka, Japan; a part interest

[21] Appl. No.: 148,912

[22] Filed: Nov. 5, 1993

[30] Foreign Application Priority Data

Nov. 6, 1992 [JP] Japan ................. 4-322521

[51] Int. Cl.⁶ .............................. A61M 16/00
[52] U.S. Cl. ...................... 128/207.15; 128/207.14
[58] Field of Search ............. 128/207.14, 207.15, 128/200.26; 604/101

[56] References Cited

U.S. PATENT DOCUMENTS

| | | | |
|---|---|---|---|
| 3,841,319 | 10/1974 | Michael et al. | 601/41 |
| 4,090,518 | 5/1978 | Elam | 128/207.15 |
| 4,091,816 | 5/1978 | Elam | 128/207.15 |
| 4,230,108 | 10/1980 | Young | 128/207.15 |
| 4,231,365 | 11/1980 | Scarberry | 128/207.15 |
| 4,235,239 | 11/1980 | Elam | 128/207.15 |
| 4,327,720 | 5/1982 | Bronson et al. | 128/207.15 |
| 4,334,534 | 6/1982 | Ozaki | 128/207.15 |
| 4,497,318 | 2/1985 | Donmichael | 128/207.15 |
| 4,509,514 | 4/1985 | Brain | 128/207.15 |
| 4,688,568 | 8/1987 | Frass et al. | 128/207.15 |
| 4,791,923 | 12/1988 | Shapiro | 128/207.15 |
| 5,259,371 | 11/1993 | Tonrey | 128/207.15 |

FOREIGN PATENT DOCUMENTS 0092618 2/1983 European Pat. Off. .

*Primary Examiner*—Edgar S. Burr
*Assistant Examiner*—Aaron J. Lewis

[57] ABSTRACT

An emergency resuscitation endoesophageal airway comprises an arch-shaped respiration tube closed at a distal end but opened at a proximal end; a first inflatable balloon of a rubber-like elastic material attached to the respiration tube at a position close to the distal end thereof for closing an esophagus of a patient; a second inflatable balloon of a flexible synthetic resin attached to the respiration tube at a position spaced from the proximal end thereof for closing a pharynx of the patient; and first and second inflating tubes for inflating the first and second inflatable balloons. The respiration tube is provided with air holes between the first and second inflatable balloons but rather near the second inflatable balloon, and the second inflatable balloon is so designed as to expand in both longitudinal and radial directions to an extent much greater than the first inflatable balloon.

15 Claims, 5 Drawing Sheets

EMERGENCY RESUSCITATION APPARATUS

BACKGROUND OF THE INVENTION

1. Field of the Invention

The present invention relates to an emergency resuscitation apparatus and, more particularly, to an endo-esophageal airway for emergency resuscitation, used for trying artificial respiration on an emergency patient in a critical condition, while providing an artificial passage for flow of air or oxygen to the lungs of the patient.

2. Description of the Prior Art

Up to now, artificial respiration has been employed widely to resuscitate an emergency patient in a critical condition. In the most case, this is carried out by endotracheal intubation in which an endotracheal tube is inserted into the trachea of the patient through the mouth or nose of the patient and then connected to a resuscitator to introduce air or oxygen into the patient.

In the endotracheal intubation, it is primarily required to insert a laryngoscope into the cavity of the mouth to visualize the larynx. Then, a distal end of the endotracheal tube must be inserted into the trachea quickly, while observing the glottis under direct laryngoscopy. Thus, there are only limited skilled persons who can practice sufficiently controlled artificial lung ventilation by the endotracheal intubation. In fact, in a certain country, the persons qualified to practice the endotracheal intubation have been limited to those licensed to practice such medical treatments, for example, medical doctors. Further, the endotracheal intubation involves technical difficulties when it is difficult to open the mouth of the patient or when the extension of the injured cervical spines endangers the patient in cases of cranial and cervical trauma. Since the regions between the innermost depths of the pharynx and the larynx have high risks of causing nervous reflexes, there is a great danger that the endotracheal intubation provides side effects such as arrhythmia, cardiac arrest, vomiting, laryngeal spasm, or the like when applied to a serious case whose respiratory function has been stopped.

In addition, the ciliated epitheliums of the trachea are very fragile to trauma or stresses. For example, they are weak in resistance to a pressure applied by a tube, a cuff, or a balloon, or get burnt easily by inhalation of hot air at a fire. Recently, therefore, there is a growing tendency to avoid breathing controls accomplished by inserting foreign substances into such delicate and fragile tracheae for a long time of period, as much as possible.

Recently, it has been proposed to use an esophageal obstructor airway (EOA) because of the fact that a respiration tube closed at one end will in all probability be introduced into the esophagus through the pharynx by inserting it blindly through the mouth of the patient along a median line without performing overextension of the larynx. The esophageal obstructor airways (EOA) are now employed in some countries including the United States of America, Canada and Japan as an emergency resuscitation apparatus. Such an apparatus generally comprises a respiration tube having a closed distal end and a proximal open end and being provided with air holes in a middle part of a side wall thereof, an inflatable balloon arranged near the distal end of the respiration tube, a slender elongated inflation tube connected to the inflatable balloon, and a face mask fixed to the open end of the respiration tube.

The artificial lung ventilation is carried out in the following manner: Firstly, the distal end of the respiration tube is inserted into the low esophagus of a patient through the mouth. Then, the inflatable balloon is inflated by supplying air through the inflation tube to bring it into close contact with the esophageal wall, and the face-mask is brought into close contact with the face of the patient. The open end of the respiration tube is connected to a lung ventilator or a resuscitator to practice positive pressure artificial respiration on the patient. The air fed to EOA flows out of the respiration tube into the trachea through the air holes. Since the esophagus is blocked by the balloon, the air does not flows into the stomach, but flows into the trachea via the pharynx and glottis, and then into the lungs of the patient. The air in the lungs is then exhaled in the reversed course by releasing the pressure. This process ensures easy and rapid intubation, but it has to be assisted by an assistant to hold the mask in close contact with the face of the patient. In addition, a location of the distal end of the respiration tube put in the esophagus cannot be adjusted at will, sometimes resulting in failure in obstruction by the inflated balloon. Further, it is difficult to hold close contact between the mask and the face of the patient during transport within an ambulance.

On the other hand, there have been used laryngeal mask airways (LMA) imported from the United Kingdom, which has a structure as shown in FIG. 5. Such a laryngeal mask airway comprises a hollow respiration tube 101 like a short endotracheal tube, a cushion mask 102 mounted on one open end of the tube 101 and having an inflatable ring-like cushion 103 attached thereto, and means 105 for inflating the ring-like cushion 103. In use, the cushion 103 is deflated to minimize its volume and then inserted from the cavity of the mouth toward the larynx along the median line until the cushion 103 is stopped around the area between the pharynx and larynx. In this position, the cushion 103 is inflated by introducing a certain amount of air through the inflating means 105 and brought into close contact with the laryngeal opening, thereby closing the uppermost part of the esophagus and preventing the flow of air into the stomach. Under such a condition, the positive pressure artificial lung ventilation is accomplished through the opposite open end 104 of the respiration tube 101.

The intubation of LMA can be carried out with ease and rapidly when the patient is under anesthesia or unconsciousness. Also, if it is easy to open the mouth of the patient because of deep anesthesia, and if the patient shows no local nervous reflex but has any spontaneous respiration, it is easy to perform the proper intubation as the respiration tube can be thrust properly by confirming the location of the distal end thereof with the breath sounds through it.

However, such an apparatus involves technical difficulties for use in emergency resuscitation. For example, it is difficult to locate the respiration tube on the proper position rapidly when the respiratory function of the patient has been stopped for some reason or other. Further, there is a fear of blockage of the airway when the cushion is inflated greatly. In addition, it is difficult to bring the cushion into close contact with the laryngeal opening because of a complex configuration of the pharynx. In case of the high positive pressure artificial ventilation, the cushion can not be brought into close contact with the laryngeal opening, thus making it difficult to prevent the flow of air into the stomach, which in turn results in failure in artificial lung ventilation.

SUMMARY OF THE INVENTION

It is therefore an object of the present invention to provide an emergency resuscitation apparatus, i.e., an endoesophageal airway for emergency resuscitation, which makes it possible to practice artificial lung ventilation easily, quickly and surely on a patient even by any person who has no physician's license to resuscitate the patients.

Another object of the present invention is to provide an endoesophageal airway for emergency resuscitation, which can be used only by inserting a respiration tube into the esophagus without use of a mask and insertion of a respiration tube into the trachea.

Still another object of the present invention is to provide an endoesophageal airway for emergency resuscitation, which makes it possible to adjust the depth of insertion of the respiration tube in the esophagus as well as to prevent flow of air into the stomach and the cavity of the mouth.

According to the present invention, these and other objects are achieved by providing an emergency resuscitation endoesophageal airway comprising an arch-shaped respiration tube closed at a distal end but opened at a proximal end; a first inflatable balloon of a rubber-like elastic material attached to the respiration tube at a position close to the distal end thereof for closing an esophagus of a patient; a second inflatable balloon of a flexible synthetic resin attached to the respiration tube at a position spaced from the proximal end thereof for closing a pharynx of the patient; first and second inflating tubes for inflating said first and second inflatable balloons, wherein said respiration tube is provided with air holes between the first and second inflatable balloons but rather near the second inflatable balloon, and wherein said second inflatable balloon is so designed as to expand in both longitudinal and radial directions to an extent much greater than the first inflatable balloon.

BRIEF DESCRIPTION OF THE DRAWINGS

These and other objects, features and advantages of the present invention will become clear from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

Figure 1:
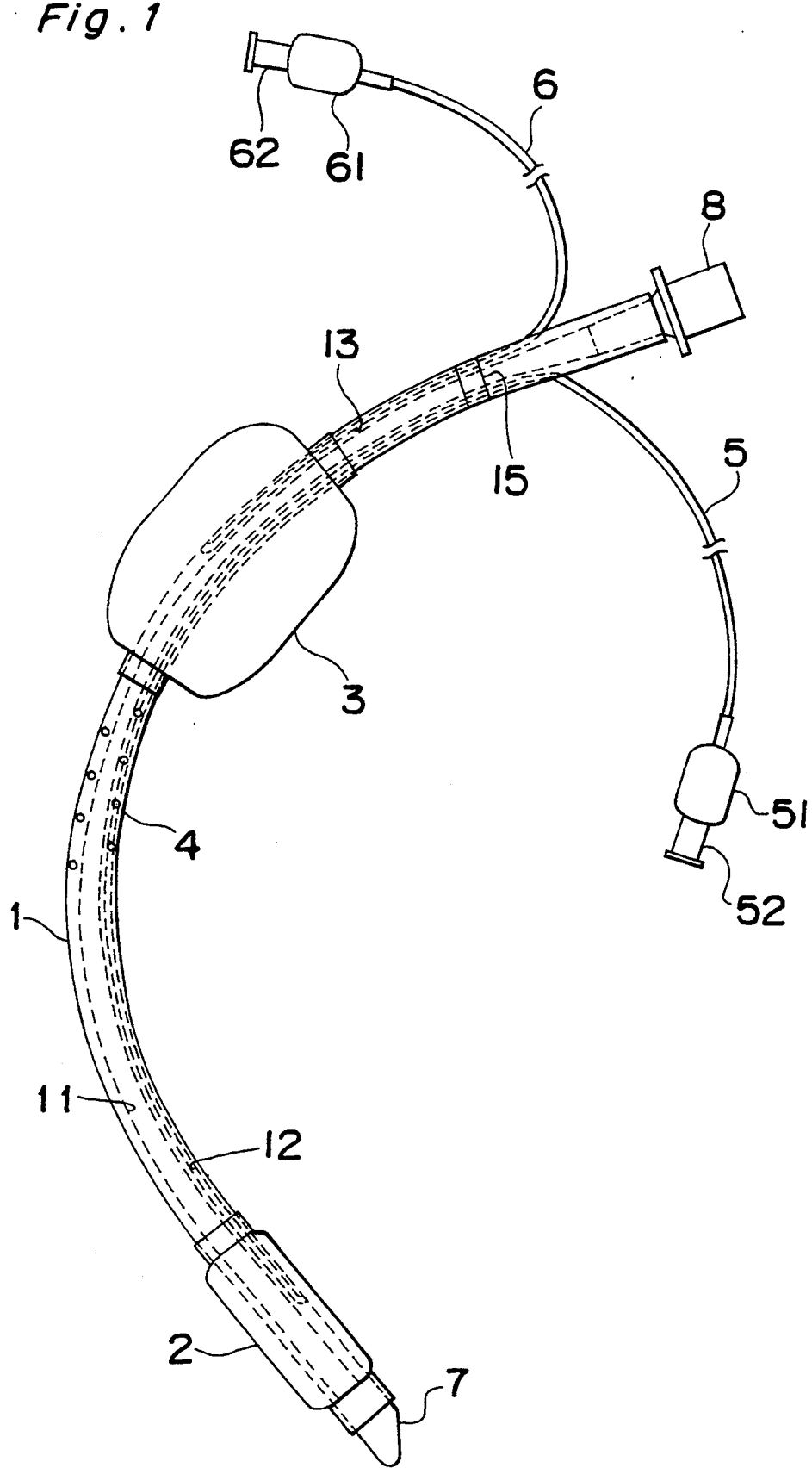
FIG. 1 is a plan view of an endoesophageal airway for emergency resuscitation according to the present invention.
Figure 2:
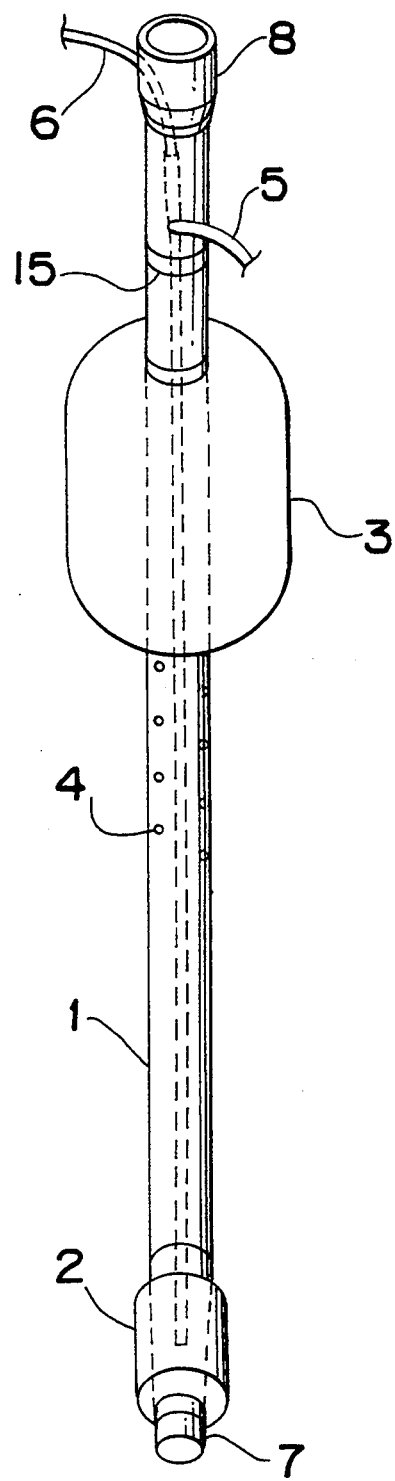
FIG. 2 is a partial side view of the endoesophageal airway for emergency resuscitation of FIG. 1.

Referring now to FIGS. 1 and 2, there is shown an endoesophageal airway for emergency resuscitation according to the present invention, which comprises a respiration tube 1 having air holes or passages 4 provided therein; a first inflatable balloon 2 arranged on the side of a distal end of respiration tube 1 for closing the esophagus; a second flexible and inflatable balloon 3 of a synthetic resin arranged on the side of a proximal end of respiration tube 1 for closing the pharynx; and inflating tubes 5 and 6 respectively connected to first and second inflatable balloons 2 and 3. The respiration tube 1 is provided with air holes 4 between first and second inflatable balloons 2 and 3 but rather near second inflatable balloon 3. Second inflatable balloon 3 is so designed as to expand in both longitudinal and radial directions to an extent much greater than the first inflatable balloon 2.

As shown in FIG. 1, the respiration tube 1 is usually made of a synthetic material having good flexibility and elasticity in the form of an arch-shaped tube curved like a bow but straightened at a leading part including first inflatable balloon 2 on the side of the distal end thereof, so that the endoesophageal airway may be inserted easily into the esophagus of a patient through the cavity of the mouth. As a typical synthetic material for respiration tube 1, there may be used those such as non-rigid polyvinyl chloride, silicone rubber, or polyurethanes.

Respiration tube 1 has a main lumen 11 and is closed at a distal end but opened at a proximal end. Main lumen 11 is used to provide an artificial airway for inhalation and exhalation of air or oxygen. To that end, respiration tube 1 is provided with a plurality of air holes 4 with a circular cross section between first and second inflatable balloons 2 and 3 but in the proximity of second inflatable balloon 3, whereby main lumen 11 is communicated with the trachea through air holes 4 when the endoesophageal airway for emergency resuscitation is properly inserted into the esophagus of the patient.

A closed part 7 of the distal end is slanted in the direction opposite to the curved direction of respiration tube 1 and rounded to provide curved corners. On the proximal end of respiration tube 1 there is provided a connector 8, usually of a synthetic resin, having a connecting portion so that the endoesophageal airway can be connected directly to a manually operated resuscitator or an automatic resuscitator (not shown). To this end, connector 8 is generally designed so as to have an outer diameter of 15 mm and a taper of 1/40, as defined internationally.

Respiration tube 1 is further provided with first and second small-sized lumens 12 and 13 in its side wall. First small-sized lumen 12 is communicated at one end thereof with first inflatable balloon 2 through an opening formed in the wall of respiration tube 1 and at the other end connected to inflating tube 5 through an opening provided in the wall of the respiration tube 1 near the proximal end thereof.

Second small-sized lumen 13 is communicated at one end thereof with second inflatable balloon 3 and at the other end to inflating tube 6 through an opening formed in the wall of respiration tube 1.

A length and a diameter of the respiration tube 1 are generally determined according to physiques of the patients, but the diameter of respiration tube 1 is so determined as to have a diameter smaller than that of the esophagus to provide a sufficient space for formation of airway between them. However, there is no need to make the respiration tube 1 to measure precisely, as compared with the endotracheal tube of the prior art. For practical use, it is sufficient to provide several respiration tubes which are different from one another in distance between the first and second balloons as each respiration tube may be applied to a few physiques.

The closed distal end of respiration tube 1 is usually formed as an integral part thereof, as shown in FIG. 1. Alternately, the closed distal end may be formed as a separate round end member having a configuration similar to that of FIG. 1 and serving as a stopper. In this case, the end member may be made of a material different from that of respiration tube 1.

Further, respiration tube 1 may be provided with an insertion mark 15 between second inflatable balloon 3 and the connecting portion of respiration tube 1 where inflating tubes 5 and 6 are connected to respiration tube 1, to make it easy to determine the depth of insertion of the endoesophageal airway for emergency resuscitation into the esophagus.

First inflatable balloon 2 is arranged on respiration tube 1 near closed distal end 7 thereof for closing the esophagus, while second inflatable balloon 3 is arranged on respiration tube 1 at a position spaced from the proximal end of respiration tube 1 for closing the pharynx.

First inflatable balloon 2 is usually made of a rubber-like elastic material such as, for example, natural rubber, synthetic rubber, and elastomers in the form of a flexible tubular membrane. Typical synthetic rubber includes isoprene rubber, silicone rubber, urethane rubber, ethylenepropylene rubber, etc. Further, as a material for first inflatable balloon 2, it is possible to use non-rigid polyvinyl chloride as it has relatively good expansibility. The flexible tubular membrane for first inflatable balloon 2 is attached to a peripheral portion, where first small-sized lumen 12 opens, of respiration tube 1 near the distal end thereof, and hermetically fixed thereto to make a gas communication between the first inflatable balloon 2 and the small-sized lumen 12 through the opening of the latter. Thus, first inflatable balloon 2 is inflated like an air-sac by feeding air through inflating tube 5 and small-sized lumen 12, whereby hermetically closing the lower part of the esophagus.

Second inflatable balloon 3 is made of a relatively soft synthetic resins such as, for example, polyethylene, polyester, non-rigid polyvinyl chloride, silicone resin, polyurethanes, etc. in the form of a cylindrical soft membrane. The cylindrical membrane is attached to a peripheral portion, where the small-sized lumen 13 is opened, of respiration tube 1 near the proximal end thereof and hermetically fixed thereto to make a fluid communication between second inflatable balloon 2 and small-sized lumen 13 through the opening of the latter. Thus, inflatable balloon 3 is inflated like an air-sac by feeding air into the small-sized lumen 13 through the inflating tube 6. In this case, the second inflatable balloon 3 is expanded in accordance with complex configurations of the pharynx and brought into light contact with the surrounding structures of the pharynx and cavity of mouth, thereby hermetically closing the space between the cavity of mouth and the upper part of the pharynx. Since inflatable balloon 3 is of a relatively soft synthetic material, it is possible to inflate the balloon 3 at a relatively low pressure without putting excess pressure upon the surrounding structures of the pharynx and the cavity of the mouth.

Second inflatable balloon 3 is made of a soft material of which the rubber-like elasticity is smaller than that of the first inflatable balloon 2 to prevent the surrounding pharyngeal structures from damage due to pressure applied by the second inflatable balloon 3. Thus, if the artificial lung ventilation is carried out under a certain pressure exceeding a contact force between second inflatable balloon 3 and the surrounding pharyngeal structures, there is a fear that the second inflatable balloon 3 may be moved from the original position by the pressure in the esophagus. To solve this problem as well as to ensure good airtightness and fixing properties of the second inflatable balloon 3, the second inflatable balloon 3 in the embodiment of FIG. 1 is so designed that it can be inflated in both longitudinal and radial directions to an extent greater than first inflatable balloon 2.

A volume of a space between second inflatable balloon 3 and the respiration tube 1 is so determined that the second inflatable balloon 3 is just filled up with air when a certain amount of air determined in accordance with a physique of a patient is supplied to the balloon 3 at a pressure of 10 cmH$_2$O or lower. In general, the amount of air sufficient to fill up the second inflatable balloon 3 is 50 to 150 ml for adults, but 30 to 60 ml for children.

First and second inflatable balloons 2, 3 are respectively connected to inflating tubes 5 and 6 with a small diameter through small-sized lumens 12, 13. Inflating tubes 5 and 6 are usually made of synthetic material such as non-rigid polyvinyl chloride, silicone rubber, polyurethanes, polyethylene, etc. Each inflating tube 5, 6 is hermetically connected at one end thereof to lumens 12 and 13 having openings formed between second inflatable balloon 3 and connector 8. At the other end, each inflating tube 5 or 6 is connected to an air supply port 52 or 62. In the proximity of each of inflating tubes 5 and 6, there is provided a pilot inflatable balloon 51 or 61 to know the inflation of inflatable balloons 2 or 3 indirectly.

Figure 4:
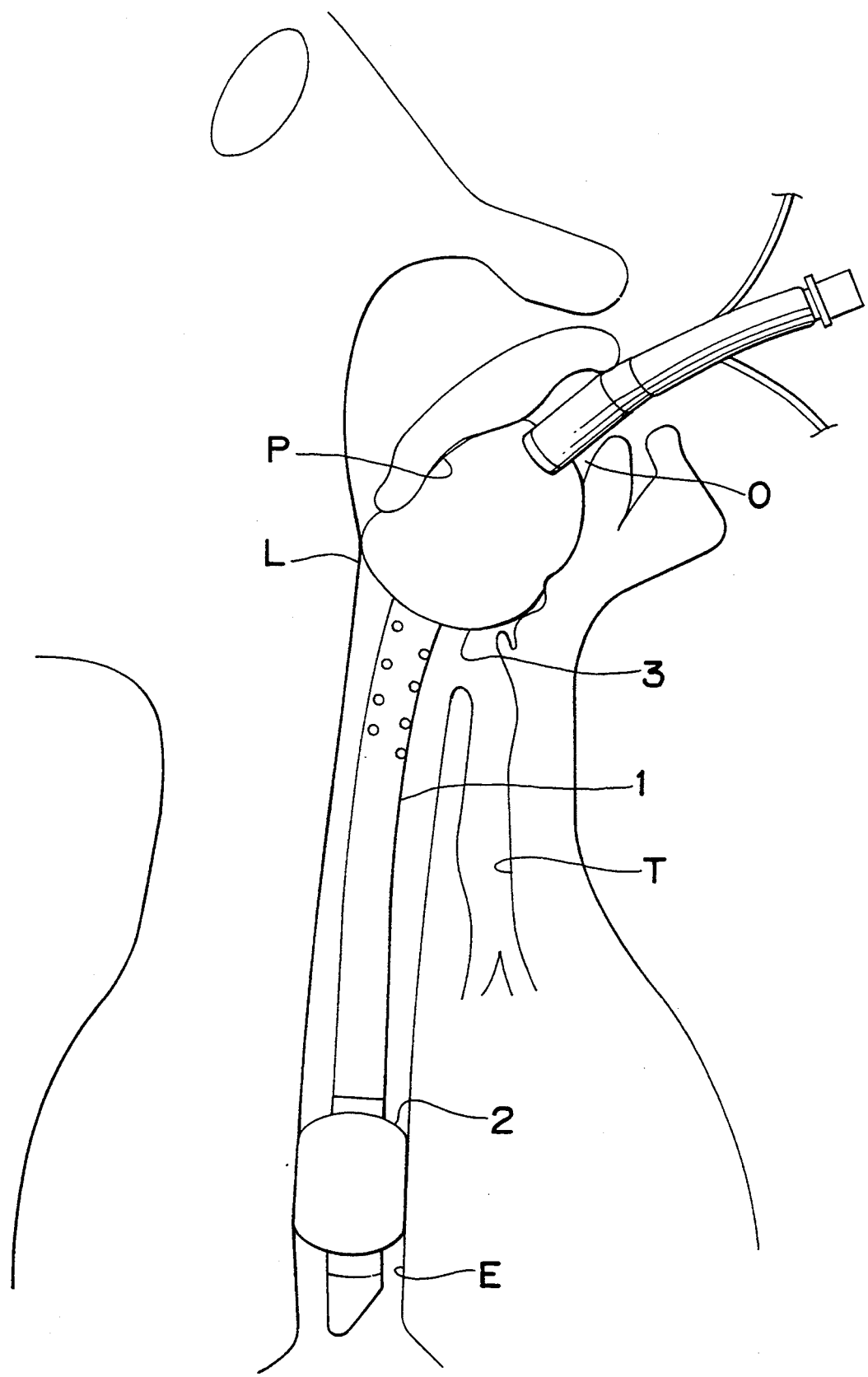
FIG. 4 is a pictorial view illustrating use of an endoesophageal airway for emergency resuscitation of the present invention, properly inserted into a patient.
Figure 5:
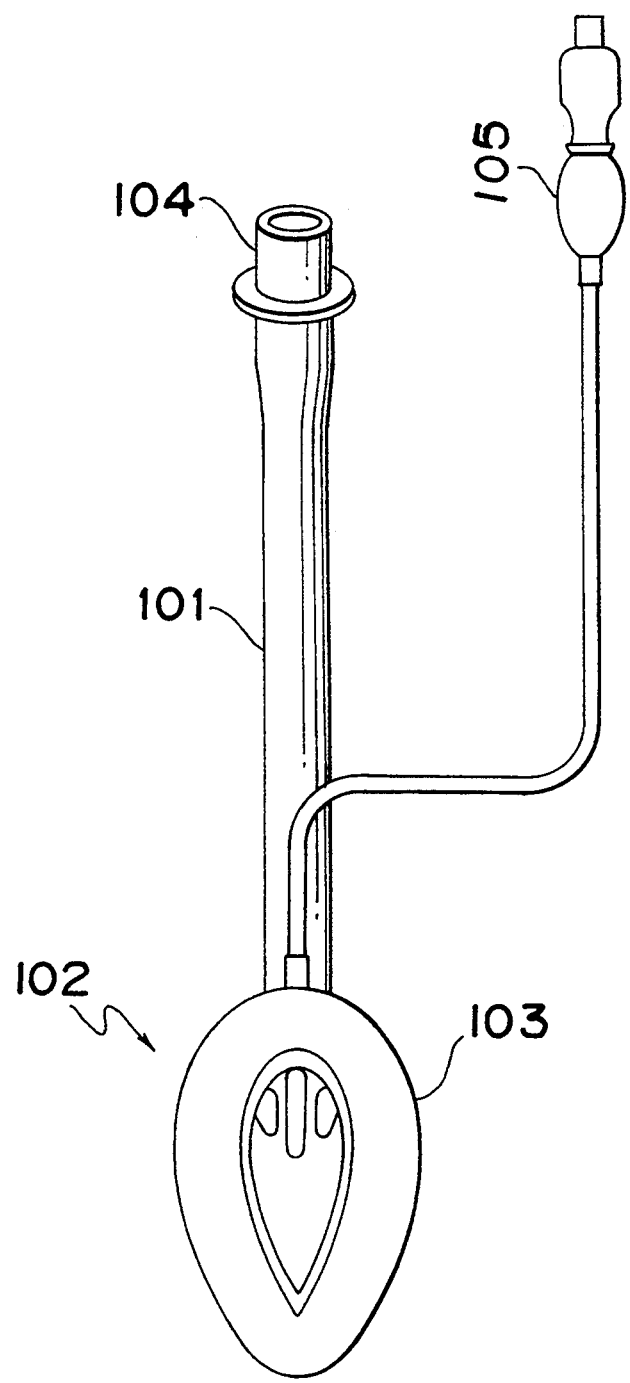
FIG. 5 is a plan view of a laryngeal mask airway according to the prior art.

In use, respiration tube 1 is introduced into the esophagus E correctly from the cavity of mouth O of the patient by inserting it into the mouth until the insertion mark is reached to the level of the lips, as shown in FIG. 4. During intubation, there is no fear of insertion of respiration tube 1 into the trachea by mistake since arch-shaped respiration tube 1 is straightened at its leading part including first inflatable balloon 2 and since the closed distal end of respiration tube 1 is slanted in the direction opposite to the curvature of respiration tube 1 and rounded to provided curved corners.

Next, the first and second inflatable balloons 2 and 3 are inflated by supplying air into the small-sized lumens 11 and 12 through respective inflating tubes 5 and 6. Thus, as shown in FIG. 4, the first inflatable balloon 2 hermetically closes the esophagus E because of its rubber-like elasticity, while second inflatable balloon 3 hermetically closes the pharynx P and larynx L. In this case, since second balloon 3 is expanded sufficiently in both longitudinal and radial directions and brought into light contact with the surrounding structures of the pharynx and cavity of the mouth, thereby hermetically closing the space between the cavity of the mouth and the upper part of the pharynx. At the same time, the endoesophageal airway is prevented from axial movement by second inflatable balloon 3.

Then, the air is fed as inhalant air from the resuscitator (not shown) to the lungs through connector 8, main lumen 11, passages 4 and the trachea. After this, the air fed to the patient is exhaled to the resuscitator through the reverse course.

Figure 3:
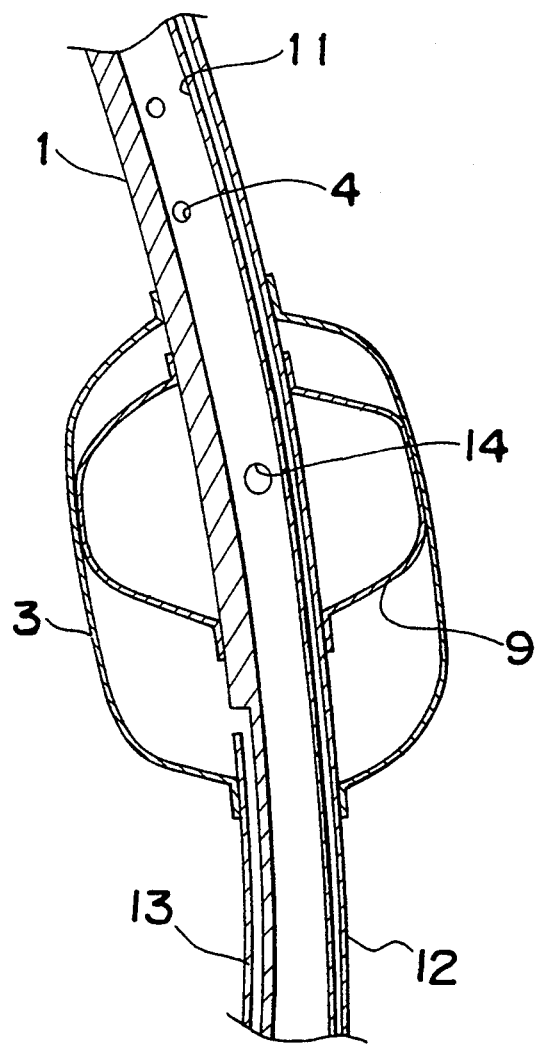
FIG. 3 is a section view of an endoesophageal airway for emergency resuscitation, illustrating another embodiment of the present invention.

Referring now to FIG. 3, there is shown another embodiment of an endoesophageal airway for emergency resuscitation, further comprising a third inflatable balloon 9 of a rubber-like elastic material. Third inflatable balloon 9 is attached to the respiration tube 1, which is covered with the second inflatable balloon 3, and communicated with the main lumen 11 of the respiration tube 1 through one or more holes 14 provided in the respiration tube 1. When the endoesophageal airway is supplied with air after properly inserting it into the esophagus of the patient, the third inflatable balloon 9 is inflated by a part of the air blown into lumen 11 of the respiration tube 1 as the air flows into the third inflatable balloon 9 through holes 14. Thus, the previously inflated second balloon 3 is additionally inflated in proportion to an internal pressure of respiration tube 1 and brought into airtight and stationary contact with the surrounding pharyngeal structures to prevent the second inflatable balloon 3 from slipping off from the surrounding pharyngeal structures.

In the embodiment of FIG. 3, the air is fed to the third inflatable balloon 9 through lumen 11 and holes 14 of respiration tube 1. Alternately, the air hole for introducing air into the third inflatable balloon 9 may be constituted by the provision of a small-sized lumen (not illustrated in the drawings) similar to small-sized lumens 12 and 13 to control the inflation of the third inflatable balloon 9 as occasion demands. In this case, the small-sized lumen is made at one end thereof open in the interior of third inflatable balloon 9 and at the other end connected to a inflating tube (not shown) similar to inflating tubes 5 and 6.

As will be understood from the above, the endoesophageal airway for emergency resuscitation of the present invention have the following advantages:

(a) It is possible to surely close the esophagus with the first inflatable balloon because of the fact that the first inflatable balloon is of a rubber-like elastic material. In addition, there is no fear of the flow of air into the esophagus nor the backward flow of contents of the stomach because of good airtightness between the first inflatable balloon and the surrounding pharyngeal structures.

(b) It is possible to close the larynx without applying excess pressure on the surrounding laryngeal structures even if the second inflatable balloon is inflated completely because of the fact that the second inflatable balloon is of a soft synthetic membrane and has size sufficiently expandable in both the longitudinal and axial directions.

(c) It is possible to insert the respiration tube into the esophagus easily without causing any risk of inserting the respiration tube into the trachea by mistake. Because, the arch-shaped respiration tube is almost straightened at its leading part including the first inflatable balloon and the closed distal end of the respiration tube is slanted in the direction opposite to the curvature of the respiration tube and rounded to provided curved corners.

(d) The respiration tube is surely introduced into the esophagus even if the respiration tube is blindly inserted into the pharynx through the mouth, thus making it possible to practice the controlled artificial lung ventilation on a patient easily by closing the larynx and the lower part of the esophagus with the first and second inflatable balloons. Thus, there is no need to get the airway with the assistance of any person.

(e) Since the esophagus is expandable and has higher adaptability to foreign substances than the trachea, the respiration tube is never required to have a precise diameter corresponding to the physiques of the patient. Thus, the present endoesophageal airway for emergency resuscitation can be applied to various persons with different physiques only by roughly adjusting the distance between the first and second inflatable balloons to that of several persons with an average physique.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An emergency resuscitation endoesophageal airway comprising:
    an arch-shaped respiration tube closed at a distal end but opened at a proximal end;
    a first inflatable balloon of an elastomeric material capable of being expanded, said first inflatable balloon being attached to the respiration tube at a position close to the distal end thereof for closing an esophagus of a patient;
    a second inflatable balloon of a flexible and relatively soft synthetic resin capable of being inflated, said second inflatable balloon being attached to the respiration tube at a position spaced from the proximal end thereof for closing a pharynx of the patient;
    first and second inflating tubes for inflating said first and second inflatable balloons, wherein said respiration tube is provided with air holes between the first and second inflatable balloons but rather near the second inflatable balloon, and wherein said second inflatable balloon is so designed as to expand in both longitudinal and radial directions to an extent much greater than the first inflatable balloon.

2. The emergency resuscitation endoesophageal airway according to claim 1, wherein the second inflatable balloon has such a high compliance that an internal space is filled with a certain amount of air supplied thereto at a pressure of 10 cmH$_2$O or lower through the second inflating tube.

3. The emergency resuscitation endoesophageal airway according to claim 1, further comprising a third inflatable balloon attached to the respiration tube but within the second inflatable balloon and in communication with a lumen of the respiration tube through one or more holes provided therein, whereby when air is introduced with pressure into the lumen of said respiration tube, the third inflatable balloon is inflated radially to an extent greater than the second inflatable balloon to cause additional inflation of the second inflatable balloon.

4. The emergency resuscitation endoesophageal airway according to claim 1, wherein said arch-shaped respiration tube is straightened at a leading part thereof including the distal end thereof and the first inflatable balloon.

5. The emergency resuscitation endoesophageal airway according to claim 1, wherein the closed distal end of said respiration tube is slanted in the direction opposite to the curvature of the respiration tube and rounded to provide curved corners.

6. The emergency resuscitation endoesophageal airway according to claim 1, wherein said respiration tube is provided with an insertion mark between said second inflatable balloon and a connecting portion of the respiration tube where said inflating tubes are connected to the respiration tube.

7. An emergency resuscitation endoesophageal airway comprising:
   an arch-shaped respiration tube closed at a distal end but opened at a proximal end, the closed distal end of said respiration tube being slanted in the direction opposite to the curvature of the respiration tube and rounded to provide curved corners;
   a first inflatable balloon of an elastomeric material capable of being expanded, said first inflatable balloon attached to the respiration tube at a position close to the distal end thereof for closing an esophagus of a patient;
   a second inflatable balloon of a flexible synthetic resin, said second inflatable balloon being attached to the respiration tube at a position spaced from the proximal end thereof for closing a pharynx of the patient; and
   first and second inflating tubes for inflating said first and second inflatable balloons, wherein said respiration tube is provided with air holes between the first and second inflatable balloons but rather near the second inflatable balloon, and wherein said second inflatable balloon is designed so as to expand in both longitudinal and radial directions to an extent much greater than the first inflatable balloon.

8. The emergency resuscitation endoesophageal airway according to claim 7, further comprising a third inflatable balloon of an elastic material capable of being expanded, said third inflatable balloon being attached to the respiration tube and positioned within the second inflatable balloon and communicated with a lumen of the respiration tube through one or more holes provided therein, whereby when air is introduced with pressure into the lumen of said respiration tube, the third inflatable balloon is inflated radially to an extent greater than the second inflatable balloon to cause additional inflation of the second inflatable balloon.

9. The emergency resuscitation endoesophageal airway according to claim 7, wherein said arch-shaped respiration tube is straightened at a leading part thereof including the distal end thereof and the first inflatable balloon.

10. The emergency resuscitation endoesophageal airway according to claim 7, said respiration tube being made of a synthetic material selected from the group consisting of non-rigid polyvinyl chloride, silicone rubber and polyurethanes.

11. The emergency resuscitation endoesophageal airway according to claim 7, wherein said respiration tube has a main lumen closed at a distal end but opened at a proximal end to provide an artificial airway for inhalation and exhalation of air or oxygen.

12. The emergency resuscitation endoesophageal airway according to claim 7, wherein said respiration tube has first and second small-sized lumens provided in a side wall thereof, said first small-sized lumen being communicated at one end thereof with said first inflatable balloon through an opening formed in the wall of the respiration tube and at the other end connected to an inflating tube through an opening provided in the wall of the respiration tube near the proximal end thereof, said second small-sized lumen is communicated at one end thereof with said second inflatable balloon and at the other end to the inflating tube through an opening formed in the wall of the respiration tube.

13. The emergency resuscitation endoesophageal airway according to claim 7, wherein the first inflatable balloon is made of an elastic material selected from the group consisting of natural rubber, synthetic rubber, elastomers, and non-rigid polyvinyl chloride.

14. The emergency resuscitation endoesophageal airway according to claim 7, wherein the first inflatable balloon is made of a synthetic rubber selected from the group consisting of isoprene rubber, silicone rubber, urethane rubber and ethylenepropylene rubber.

15. The emergency resuscitation endoesophageal airway according to claim 7, wherein the second inflatable balloon is made of a relatively soft synthetic resin selected from the group consisting of polyethylene, polyester, non-rigid polyvinyl chloride, silicone resin and polyurethane.

* * * * *